March 16, 1943. F. MEILLAND Plant Pat. 574
ROSE PLANT
Filed May 14, 1942
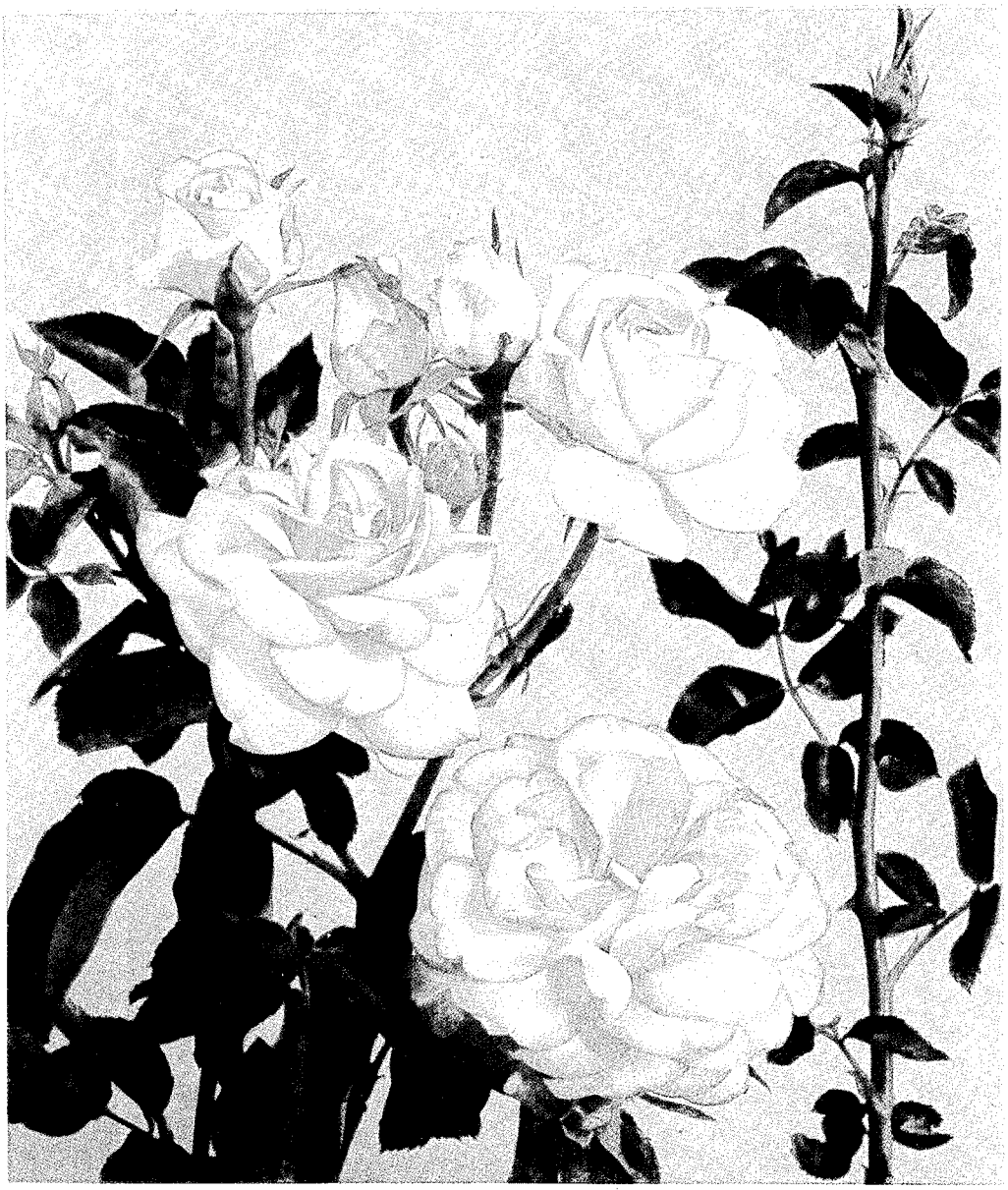
Inventor
Francis Meilland
By Robb & Robb
Attorneys Patented Mar. 16, 1943

Plant Pat. 574

UNITED STATES PATENT OFFICE

574

ROSE PLANT

Francis Meilland, Tassin-les-Lyon, France, assignor to The Conard-Pyle Company, West Grove, Pa.

Application May 14, 1942, Serial No. 442,958

1 Claim. (Cl. 47—61)

The present invention relates to a new and distinct variety of rose plant of the hybrid tea class.

This new variety originated as a seedling from cross hybridizing having as its objective to obtain a combination of features which would effect attractiveness whether the plant was utilized for cut flower purposes or garden decoration. As a result, I believe I have produced a rose which is without parallel in the combination of the following effects: A type of coloring of the blooms entirely unique and striking beyond anything previously obtained, combined with an efflorescence that gives to the plant almost a blanket effect of coloring, together with compactness of growth and abundance of foliage, which lend themselves to the enhancement of the effect referred to.

Reproduction so far has been by budding only and from this the features above and later to be referred to have been proved to be established.

The following is a detail description of the new variety, color terminology being in accord with Ridgway's Color Standard:

Type: Hardy; bush; outdoor; seedling; for cut flowers and garden decoration.

Class: Hybrid tea.

Propagation: Holds its distinguishing characteristics through succeeding propagations by budding.

*Flower*

Locality where grown: West Grove, Pennsylvania.

Flowers borne: Singly and several to stem, on normal, medium long stems.

Bloom: Abundant; outdoors.

low, Plate IV, shading towards edge to Baryta Yellow, Plate IV, and edged Tyrian-Rose, Plate XII.

*Opening.*—Opens up well.

Bloom:

*Size, when fully open.*—Two and three-fourths to three inches.

*Petalage.*—Double; from thirty-five to forty petals; arranged regularly.

*Form.*—Cupped at first, becoming flat; petals remaining at first loosely cupped inward and outward; becoming later, at maturity, loosely flat rolled outward.

Petals: Thick; soft; inside and outside, satiny.

*Shape.*—Outside—obovate with apex flat. Intermediate—obovate with apex flat. Inside—oval with apex flat with one notch.

This description of a newly opened flower was made from a rose grown outdoors in the month of August, 1941, at West Grove, Pennsylvania:

Color.—Outside petal: outside surface—Pinard Yellow, Plate IV, edged Pomegranate Purple, Plate XII; inside surface—Pinard Yellow, Plate IV, heavily edged Tyrian Rose, Plate XII. Intermediate petal: outside surface—Pinard Yellow, Plate IV, thread edged Tyrian Rose, Plate XII; Inside surface—Lemon Chrome, Plate IV, heavily edged Tyrian Rose, Plate XII. Inner petal: outside surface—Pinard Yellow, Plate IV, thread edged Tyrian Rose, Plate XII; inside surface—Lemon Chrome, Plate IV, heavily edged Tyrian Rose, Plate XII.

This description was made from a rose that was open for three days outdoors in the month

*Stem.*—Short but adheres strongly to stone like J. H. Hale peach.

*Skin.*—Medium in thickness and toughness. Tenacious to flesh with no tendency to cracking. The color is yellow in background but usually completely covered with red. No pubescence.

*Flesh.*—Yellow in color except for red at pit margin with yellow fibres. Only moderate amygdalin content and dries satisfactorily with little discoloration without use of sulphur. Texture medium to firm but melting with only a few rather fine fibres. Ripens evenly and uniformly, not becoming soft at apex prematurely as in many nectarine varieties. Flavor, slightly subacid, mild and vinous. Aroma is distinct. Eating quality very good to best.

Stone: Free.

*Fibres.*—Short and free.

*Size.*—Medium, averaging about 1⅓ inches in length, one inch in breadth, and ¾ inch in thickness.

*Form.*—Obovoid, cuneate toward base.

*Base.*—Straight. Hilum—oval. Apex—acute.

*Sides.*—Equal with surfaces regularly furrowed and ridged throughout.

*Ridges.*—Jagged with angular pits.

*Ventral edge.*—Thick with wing toward base.

*Dorsal edge.*—Full with deep groove. Ridges are interrupted on either side.

*Color of stone.*—Yellowish red becoming brown with age.

*Tendency to split.*—Very slight in any season yet encountered.

Use: Market, local, dessert, culinary, and drying.

*Keeping quality.*—Good.

*Resistance to insects.*—Good, particularly to thrips.

*Resistance to diseases.*—Medium. About as susceptible to curl and peach blight as Elberta, but more susceptible to brown rot at blooming time. Almost immune to mildew of both leaves and fruit.

*Shipping qualities.*—Medium to good about like Elberta but not so good as J. H. Hale peach or Kim nectarine. Both growers and packers are demanding it for planting and shipping.

I claim:

A new and distinct variety of nectarine substantially as described, having unusual eating and shipping qualities and which makes an attractive dried product without the use of sulphur.

FREDERIC W. ANDERSON.